US012773270B2

(12) United States Patent
Hornecker et al.

(10) Patent No.: US 12,773,270 B2
(45) Date of Patent: Oct. 27, 2026

(54) TRANSFORMATION SELECTION TECHNIQUE BASED ON TRACKER MOVEMENT

(71) Applicant: Stryker European Operations Limited, Carrigtwohill (IE)

(72) Inventors: Patrick Hornecker, Eichstetten (DE); Renu Khorwal, New Delhi (IN); Lars Fischer, Freiburg (DE); Carinne Granchi, Ashburn, VA (US)

(73) Assignee: Stryker European Operations Limited, Carrigtwohill (IE)

( * ) Notice: Subject to any disclaimer, the term of this patent is extended or adjusted under 35 U.S.C. 154(b) by 478 days.

(21) Appl. No.: 18/231,312

(22) Filed: Aug. 8, 2023

(65) Prior Publication Data

US 2025/0049509 A1 Feb. 13, 2025

(51) Int. Cl.
*A61B 34/20* (2016.01)
*A61B 6/03* (2006.01)
(Continued)

(52) U.S. Cl.
CPC .............. *A61B 34/20* (2016.02); *A61B 6/032* (2013.01); *G06T 7/70* (2017.01); *G16H 30/20* (2018.01);
(Continued)

(58) Field of Classification Search
CPC . A61B 34/20; A61B 6/032; A61B 2034/2055; A61B 2090/374;
(Continued)

(56) References Cited

U.S. PATENT DOCUMENTS 6,490,475 B1 12/2002 Seeley et al.
6,666,579 B2 12/2003 Jensen
(Continued)

FOREIGN PATENT DOCUMENTS

DE 60128722 T2 1/2008
DE 102008035736 B4 4/2013
(Continued)

OTHER PUBLICATIONS

English language abstract for DE 60 128 722 T2 extracted from espacenet.com database on Aug. 8, 2023, 2 pages.
(Continued)

*Primary Examiner* — Serkan Akar
*Assistant Examiner* — Jason P Gross
(74) *Attorney, Agent, or Firm* — Howard & Howard Attorneys PLLC

(57) ABSTRACT

A method for selecting a transformation between a pose of a tracker and a coordinate system associated with image data acquired by a medical imaging apparatus is provided. The method is performed by a processor and comprises: obtaining tracking information indicative of a plurality of different poses of a tracker that is fixedly positioned relative to a movable portion of a medical imaging apparatus; determining, based on the obtained tracking information, a movement of the tracker; and selecting, based on the determined movement of the tracker, one of a plurality of transformations between a pose of the tracker and a coordinate system associated with image data acquired by the medical imaging apparatus. A corresponding system and non-transitory computer-readable storage medium are also provided.

19 Claims, 5 Drawing Sheets

(51) Int. Cl.
*G06T 7/70* (2017.01)
*G16H 30/20* (2018.01)

(52) U.S. Cl.
CPC ................. *A61B 2034/2055* (2016.02); *G06T 2207/30241* (2013.01)

(58) Field of Classification Search
CPC .... A61B 2034/2048; A61B 2034/2051; A61B 2090/376; A61B 2090/3764; A61B 2090/378; A61B 6/4441; A61B 2034/2065; G06T 7/70; G06T 2207/30241; G06T 7/30; G06T 7/20; G06T 19/003; G16H 30/20
See application file for complete search history.

(56) References Cited

U.S. PATENT DOCUMENTS

| | | | |
|---|---|---|---|
| 8,104,957 B2 | | 1/2012 | Maier et al. |
| 11,253,216 B2 | | 2/2022 | Crawford et al. |
| 2008/0285724 A1 | * | 11/2008 | Dehler ................... A61B 6/547 378/205 |
| 2011/0164721 A1 | | 7/2011 | Jank et al. |
| 2013/0066196 A1 | | 3/2013 | Graumann et al. |
| 2020/0121267 A1 | * | 4/2020 | Deutschmann ........ A61B 6/035 |
| 2021/0169577 A1 | * | 6/2021 | Hornecker ............. A61B 34/20 |
| 2021/0330273 A1 | * | 10/2021 | Crawford ............. A61B 6/4441 |
| 2022/0301199 A1 | | 9/2022 | Tomas Fernandez et al. |
| 2023/0008419 A1 | | 1/2023 | Wilson et al. |
| 2024/0138927 A1 | * | 5/2024 | Krull ...................... A61B 34/20 |

FOREIGN PATENT DOCUMENTS

| | | | | |
|---|---|---|---|---|
| EP | 2098168 B1 | | 11/2010 | |
| EP | 4014873 A1 | * | 6/2022 | ........... A61B 6/5264 |

OTHER PUBLICATIONS

English language abstract for DE 10 2008 035 736 B4 extracted from espacenet.com database on Aug. 8, 2023, 2 pages.
English language abstract for EP 2 098 168 B1 extracted from espacenet.com database on Aug. 8, 2023, 1 page.

* cited by examiner

TRANSFORMATION SELECTION TECHNIQUE BASED ON TRACKER MOVEMENT

TECHNICAL FIELD

The present disclosure generally relates to a method for selecting a transformation between a pose of a tracker and a coordinate system associated with image data acquired by a medical imaging apparatus. A system, a computer program and a carrier such as a non-transitory computer storage medium are also provided.

BACKGROUND

In surgical navigation procedures, image data acquired by a medical imaging apparatus such as an X-ray apparatus comprising a C-arm may need to be registered to a tracker tracked by a tracking system. Such a registration may be based on a transformation between a pose of the tracker and a coordinate system associated with the image data.

In current solutions, the tracker may be fixedly positioned relative to the medical imaging apparatus, which means the transformation may be the same as long as the tracker is positioned in the same pose relative to the medical imaging apparatus. In other words, a tracker may only be arranged in a single predefined pose relative to a medical imaging apparatus and a single predefined transformation between the single predefined pose of the tracker and the coordinate system of the image data acquired by the medical imaging apparatus may be used to register the image data to the tracker.

Depending on the surgical scenario, visibility of a tracker arranged on the medical imaging apparatus by the tracking system may be limited, for example due to medical machines being arranged between a camera of the tracking system and the medical imaging apparatus. Due to this and other reasons, it may be desirable to arrange the tracker in a pose differing from the aforementioned single predefined pose. Such an arrangement may result in a different transformation between the different pose of the tracker and the coordinate system of the image data. Consequently, it may not be possible to always use the same single predefined transformation to register the image data to the tracker.

SUMMARY

There is a need for a technique that solves one or more of the aforementioned or other problems.

According to a first aspect, a method for selecting a transformation between a pose of a tracker and a coordinate system associated with image data acquired by a medical imaging apparatus is provided. The method is performed by at least one processor and comprises obtaining tracking information indicative of a plurality of different poses of a tracker that is fixedly positioned relative to a movable portion of a medical imaging apparatus. The method comprises determining, based on the obtained tracking information, a movement of the tracker. The method further comprises selecting, based on the determined movement of the tracker, one of a plurality of transformations between a pose of the tracker and a coordinate system associated with image data acquired by the medical imaging apparatus.

The method may further comprise determining, based on the determined movement of the tracker, a spatial relationship between the tracker and the movable portion.

The one transformation may be selected from the plurality of transformations based on the determined spatial relationship.

The spatial relationship may comprise a side of the movable portion at which side the tracker is arranged.

The determined movement of the tracker may be indicative of a movement direction of the tracker.

The side of the movable portion may be determined based on the movement direction of the tracker.

The side of the movable portion may be determined by selecting the side of the movable portion from a first side of the movable portion associated with a clockwise movement direction of the tracker and a second side of the movable portion associated with a counter-clockwise movement direction of the tracker.

The spatial relationship may comprise a location of the movable portion at which location the tracker is arranged.

The determined movement of the tracker may be indicative of a movement path of the tracker.

The location of the movable portion may be determined based on the movement path of the tracker.

The movable portion may be configured to move along a circle or helix.

The movement path of the tracker may comprise at least one section of a circle, ellipse or helix.

The location of the movable portion may be determined based on the at least one section of the movement path of the tracker.

The spatial relationship may comprise an orientation of the tracker relative to the movable portion.

The method may further comprise obtaining gravity information indicative of a gravitational direction.

The transformation may be selected based on the gravity information.

The movement of the tracker may be determined relative to the gravitational direction as indicated by the gravity information.

The transformation may be selected based on the movement of the tracker determined relative to the gravitational direction.

The method may further comprise obtaining at least one setup of the medical imaging apparatus selected from a start pose and an end pose of the movable portion of the medical imaging apparatus relative to an immovable portion of the medical imaging apparatus or a component having a fixed spatial relationship to the immovable portion of the medical imaging apparatus.

The transformation may be selected based on the at least one setup of the medical imaging apparatus.

The method may further comprise determining the at least one setup of the medical imaging apparatus based on the tracking information, the gravity information and the determined movement of the tracker, to obtain the at least one setup of the medical imaging apparatus.

The side of the movable portion may be determined based on the movement direction of the tracker and the obtained at least one setup of the medical imaging apparatus.

The side of the movable portion may be determined by selecting, based on the determined movement direction of the tracker and the obtained at least one setup of the medical imaging apparatus, the side of the movable portion from: a first side of the movable portion associated with (i) a clockwise movement direction of the tracker and a first setup of the medical imaging apparatus and (ii) a counter-clockwise movement direction of the tracker and a second setup of the medical imaging apparatus; and a second side of the movable portion associated with (i) a clockwise movement direction of the tracker and the second setup of the medical imaging apparatus and (ii) a counter-clockwise movement direction of the tracker and the first setup of the medical imaging apparatus.

At least two or all of the plurality of different poses of the tracker may be associated with different points in time of an image acquisition process performed by the medical imaging apparatus to acquire the image data, during which image acquisition process the movable portion of the medical imaging apparatus moves.

The medical imaging apparatus may be configured to acquire computed tomography, CT, image data.

The movable portion of the medical imaging apparatus may be part of a C-arm.

According to a second aspect, a system is provided. The system comprises at least one processor configured to perform the method according to the first aspect. The at least one processor may be configured to perform a method for selecting a transformation between a pose of a tracker and a coordinate system associated with image data acquired by a medical imaging apparatus, the method comprising: obtaining tracking information indicative of a plurality of different poses of a tracker that is fixedly positioned relative to a movable portion of a medical imaging apparatus; determining, based on the obtained tracking information, a movement of the tracker; and selecting, based on the determined movement of the tracker, one of a plurality of transformations between a pose of the tracker and a coordinate system associated with image data acquired by the medical imaging apparatus.

The system may further comprise at least one of the following entities: (i) the medical imaging apparatus comprising the movable portion and configured to acquire the image data; (ii) a tracking system, such as an optical tracking system comprising a camera, configured to provide the tracking information; (iii) a gravity sensor configured to provide the gravity information and optionally fixed to the tracking system and/or the camera; (iv) the tracker.

According to a third aspect, a non-transitory computer-readable storage medium is provided. The storage medium stores a computer program comprising instructions which, when executed by at least one processor, cause the at least one processor to perform the method according to the first aspect. The storage medium may store a computer program comprising instructions which, when executed by at least one processor, cause the at least one processor to perform a method for selecting a transformation between a pose of a tracker and a coordinate system associated with image data acquired by a medical imaging apparatus, the method comprising: obtaining tracking information indicative of a plurality of different poses of a tracker that is fixedly positioned relative to a movable portion of a medical imaging apparatus; determining, based on the obtained tracking information, a movement of the tracker; and selecting, based on the determined movement of the tracker, one of a plurality of transformations between a pose of the tracker and a coordinate system associated with image data acquired by the medical imaging apparatus.

According to a fourth aspect, a computer program is provided. The computer program comprises instructions which, when executed by at least one processor, cause the at least one processor to perform the method according to the first aspect. The computer program may be carried by a data stream or stored on a (e.g., non-transitory computer-readable) storage medium.

According to a fifth aspect, a carrier carrying the computer program of the fourth aspect is provided. The carrier may be a data stream or a (e.g., non-transitory computer-readable) storage medium.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
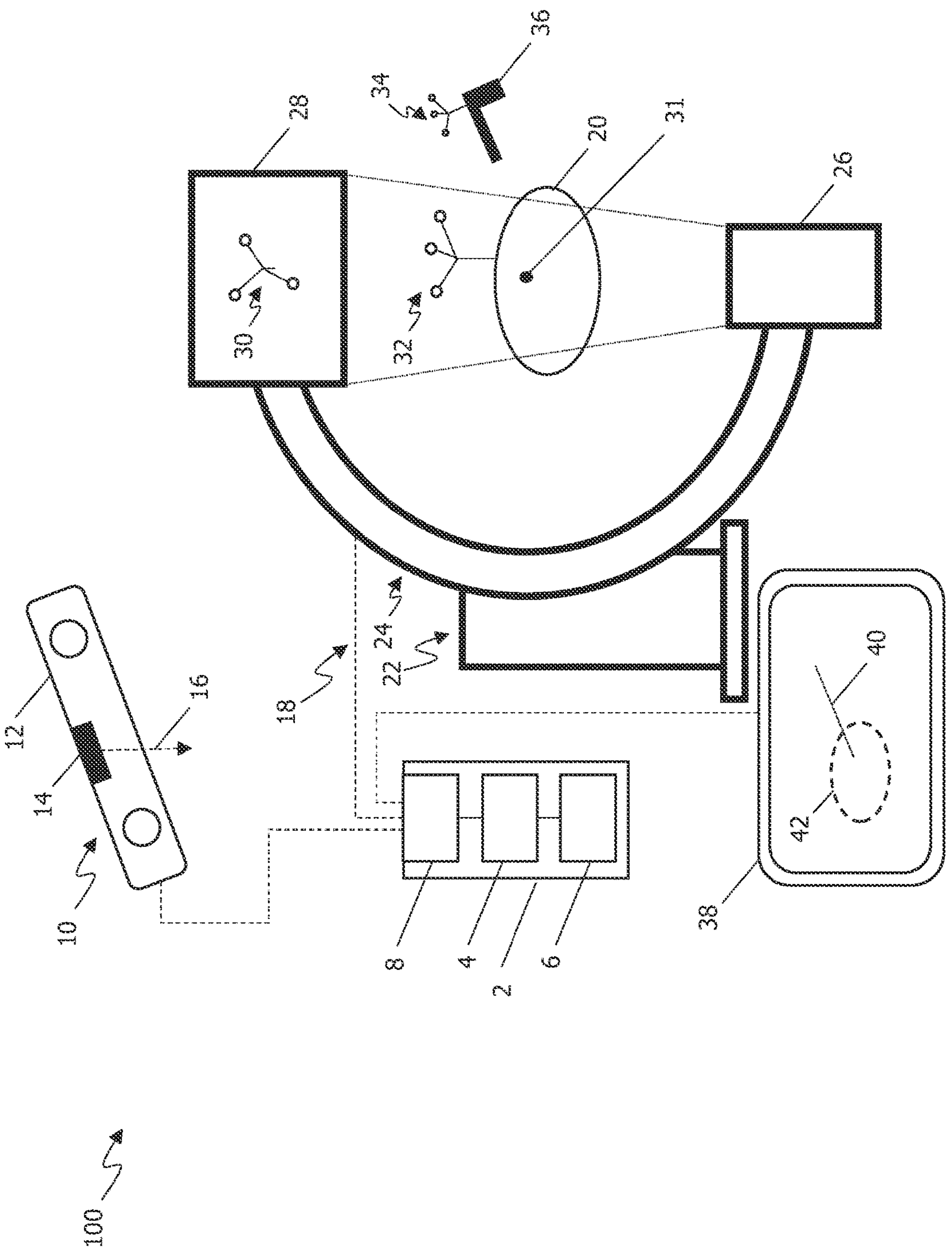
FIG. 1 shows a system in accordance with the present disclosure.

In the following, exemplary embodiments of the present technique will be explained with reference to the drawings. Unless indicated otherwise, the same reference numerals denote the same or similar structural features.

FIG. 1 shows a system 100 in accordance with the present disclosure. The system 100 may be a surgical navigation system.

The system 100 comprises a processing apparatus 2 including at least one processor 4. The at least one processor 4 is communicatively coupled to a memory 6, which is one example of a non-transitory computer-readable storage medium. The at least one processor 4 may be further communicatively coupled to an interface 8 of the apparatus 2. The apparatus 2 may be implemented as a spatially distributed processing apparatus 2, for example by implementing the at least one processor 4, the memory 6 and/or the interface on different servers (e.g., as virtual processor(s), virtual memory or memories). In other words, at least parts of the apparatus 2 may be realized by a cloud computing platform. Alternatively, the apparatus 2 may be implemented as a local processing apparatus 2 that is for example arranged in a scanning room or an operating room of a hospital.

The system 100 further comprises a tracking system 10. In the illustrated example, the tracking system 10 is an optical tracking system comprising a stereo camera 12. A gravity sensor 14 (e.g., a 3-axis accelerometer) may be fixedly arranged relative to the stereo camera 12 to obtain a gravitational direction 16. The tracking system 10 may be communicatively coupled to the at least one processor 4 via the interface 8 and may be configured provide the at least one processor 4 with tracking data indicative of tracked poses of trackers. The term "pose" as used herein is to be understood as meaning "at least one of a position and an orientation".

The system 100 further comprises a medical imaging apparatus 18 configured to acquire image data. The image data may comprise one or more medical images of a patient's body 20. The medical imaging apparatus 18 comprises an immovable (e.g., stationary) portion 22 and a movable portion 24. The movable portion 24 is configured to move relative to the immovable portion 22 when the image data is acquired by the medical imaging apparatus 18. The immovable portion 22 is configured to remain stationary (e.g., within an operating room) when the image data is acquired. The medical imaging apparatus 18 may be communicatively coupled to the at least one processor 4 via the interface 8 and may be configured to provide the at least one processor 4 with the acquired image data. In the illustrated example, the medical imaging apparatus 18 is configured to acquire a computed tomography, CT, image of the patient's body 20 as the image data and comprises a C-arm, having an X-ray source 26 and an X-ray detector 28, as movable portion 24, and a cart as stationary portion 22. The C-arm is configured to rotate around a center point 31, also referred to as isocenter, when acquiring the CT image, also referred to as CT scan.

The system 100 further comprises one or more trackers 30-34. The tracker 30 is fixedly positioned relative to the movable portion 24 of the medical imaging apparatus 18, in the illustrated example directly attached to the X-ray detector 28, and may thus be referred to as medical imaging apparatus tracker. The tracker 32 is spatially fixed relative to the patient's body 20, for example adhesively attached to the patient's skin, and may thus be referred to as patient tracker. The tracker 34 is attached to a medical instrument 36 handled by a surgeon or a surgical robot, and may thus be referred to as medical instrument tracker. Each of the trackers 30-34 can be tracked by the tracking system 10, which means the tracking system 10 can determine the pose of each of the trackers 30-34 in a (e.g., real-world) tracking coordinate system. The (e.g., origin and orientation of the) tracking coordinate system may be defined by one of the trackers, for example by the patient tracker 32. The tracking system 10 may be configured to provide the at least one processor 4 with information indicative of the tracked poses of the trackers 30-34, for example in the tracking coordinate system. In the illustrated example, each of the trackers 30-34 comprises a plurality of optical tracking markers detectable by the stereo camera 12, but the present disclosure is not limited thereto.

The system 100 further comprises a display unit 38. The display unit 38 may be communicatively coupled to the at least one processor 4 via the interface 8. A navigation view may be displayed by the display unit 38, indicating a tracked pose of the medical instrument 36 relative to representation of the patient's body 20, for example by overlaying a trajectory 40 onto a medical image 42 of the patient's body 20, the medical image being included in the image data acquired by the image acquisition apparatus 18.

To this end, a transformation between the tracking coordinate system and a coordinate system associated with the image data (e.g., associated with or defined by one or more images comprised in the image data, such as the medical image 42) may be required. The coordinate system associated with the image data may be defined by the isocenter 31 having a fixed spatial relationship to the X-ray detector 28. More generally speaking, the coordinate system associated with the image data may have a (e.g., predefined) spatial relationship relative to the movable portion 24 of the medical imaging apparatus 18.

According to the present disclosure, the tracker 30 can be mounted on the movable portion 24 in two or more predefined poses. This means that the relative pose between the tracker 30 and the movable portion 24 may differ from one image acquisition process to another, so the respective transformation between the pose of the tracker 30 and the coordinate system associated with the respective image data also differ between different instances of acquired image data. The technique disclosed herein may enable an automatic selection of a suitable transformation from a plurality of transformations. This approach will now be described in detail. Although the reference signs used in FIG. 1 will be used in the following, this is not to be understood as necessarily limiting the features described in the following to the respective features shown and described for FIG. 1.

Figure 2:
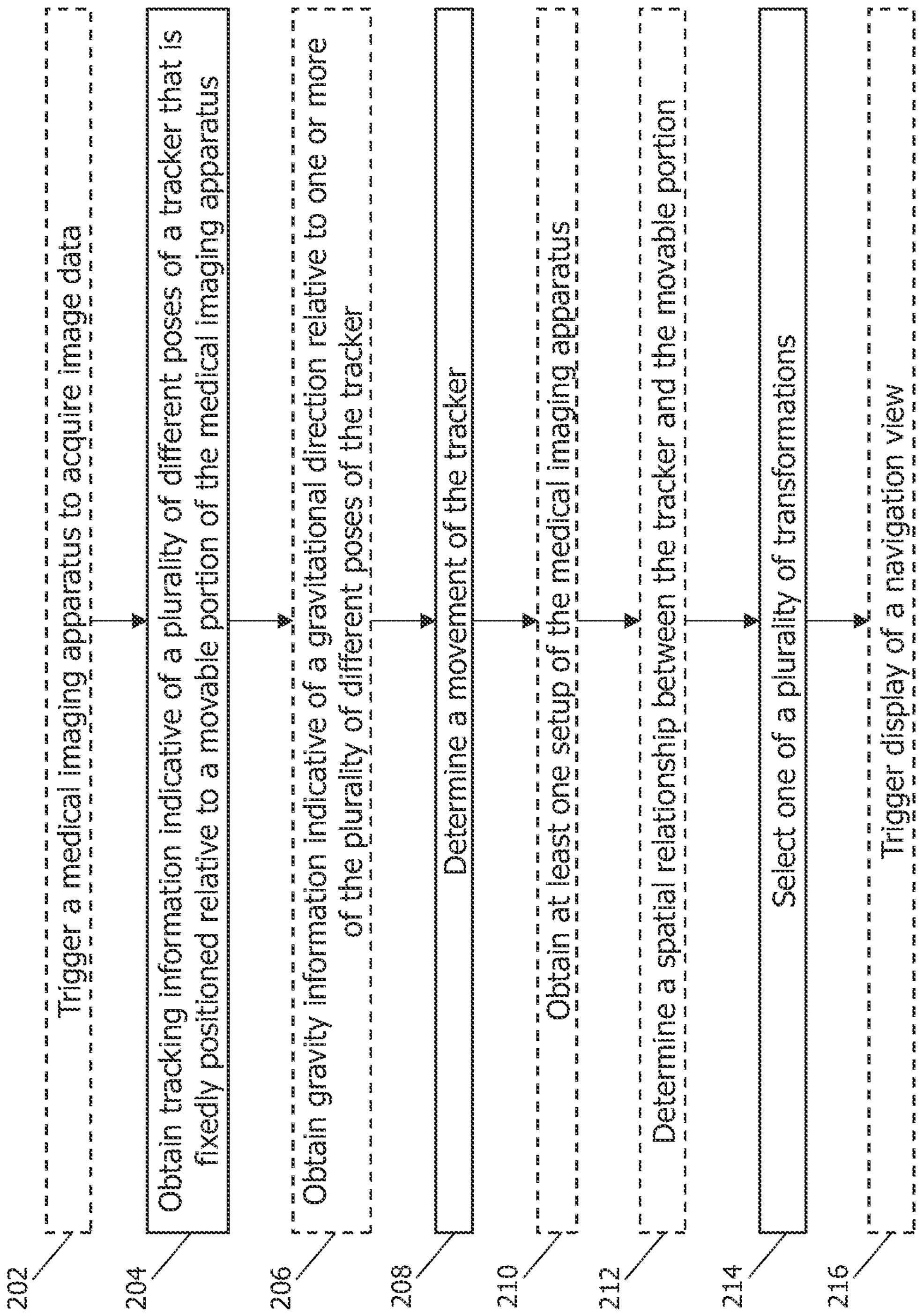
FIG. 2 shows a method in accordance with the present disclosure.

FIG. 2 shows a method in accordance with the present disclosure. The method may be performed by the at least one processor 4. The memory 6 may store a computer program comprising instructions which, when executed by the at least one processor 4, cause the at least one processor 4 to perform the method of FIG. 2.

In optional step 202, the medical imaging apparatus 18 is triggered to acquire image data.

Step 202 may comprise triggering the medical imaging apparatus 18 to acquire the image data by performing an image acquisition process during which the movable portion 24 moves.

At least steps 202-214 of the method disclosed herein may be performed before scanning a patient's body 20. Nevertheless, in some scenarios, it may be desirable that the image data acquired by the medical imaging apparatus 18 when triggered accordingly in step 202 comprises a representation of at least a portion of the patient's body 20.

The image data may comprise or be medical image data. The image data may comprise one or more medical images (e.g., images acquired using a medical imaging technique). The image data may comprise three-dimensional image data. The image data may be acquired by the medical imaging apparatus 18 while the movable portion 24 moves relative to the immovable portion 22. The image data may comprise a computed tomography, CT, image, also referred to as CT scan. The image data may comprise a cone-beam CT, CBCT, scan. The image data may comprise a spiral CT scan or a multi-column CT scan. The image data may comprise one or more single-spectrum or multi-spectral images. The image data may comprise one or more three-dimensional images. The image data may comprise one or more images acquired by the medical imaging apparatus 18 while the movable portion 24 moves relative to the immovable portion 22.

In step 204, tracking information is obtained.

The tracking information is indicative of a plurality of different poses of the tracker 30 that is fixedly positioned relative to the movable portion 24 of the medical imaging apparatus 18. The tracker 30 may be directly attached to the movable portion 24 or attached to the movable portion 24 via a mounting assembly arranged on the movable portion 24. At least one of the movable portion 24, the mounting assembly and the tracker 30 may be configured such that the tracker 30 can be fixedly positioned relative to the movable portion 24 in two or more (e.g., predefined) poses. The movable portion 24 may comprise multiple (e.g., opposing) sides (e.g., two or more of a left side, a right side, a front side and a rear side) at which the tracker 30 can be arranged.

The tracking information may further indicate of one or more tracked poses of the tracker 32 and/or 34. One or more of the poses indicated by the tracking information may be indicated relative to a similar coordinate system such as the tracking coordinate system.

At least two or all of the plurality of different poses of the tracker 30 may be associated with different points in time (e.g., one point in time per pose). The different points in time may be part of an image acquisition process performed by the medical imaging apparatus 18 to acquire the image data. The plurality of different poses of the tracker 30 may be obtained by the tracking system 10 during the image acquisition process. During that image acquisition process, the movable portion 24 of the medical imaging apparatus 18 may move relative to the immovable portion 22. Consequently, the tracker 30 may also move in space when acquiring the image data, resulting in the different tracked poses of the tracker 30.

In optional step 206, gravity information is obtained.

The gravity information may be obtained from the gravity sensor 14. The gravity information is indicative of the gravitational direction 16, for example relative to one or more of the tracked poses of the tracker(s) 30-34 (e.g., relative to one or more of the plurality of different poses of the tracker 30). The tracking coordinate system (e.g., an orientation thereof) may be defined based on the gravitational direction 16. One or more, for example all, of the tracked poses of the tracker(s) 30-34 may be defined relative to the gravitational direction.

In step 208, a movement of the tracker 30 is determined.

The movement of the tracker 30 is determined based on at least the obtained tracking information.

The movement of the tracker 30 may be determined relative to the gravitational direction 16 as indicated by the gravity information.

The determined movement of the tracker 30 may be indicative of a movement direction of the tracker 30, for example a clockwise or a counter-clockwise movement direction (e.g., as observed by the tracking system 10). The movable portion 24 and the tracker 30 may move in the movement direction during the image acquisition process for acquiring the image data (e.g., triggered in step 202).

The determined movement of the tracker 30 may be indicative of a movement path of the tracker 30. The movable portion 24 and the tracker 30 may move along the movement path during the image acquisition process for acquiring the image data (e.g., triggered in step 202). For example, the movable portion 24 may be configured to move along (e.g., at least a part of) a circle or helix. In this case, the movement path of the tracker 30 may comprise at least one section of a circle, ellipse or helix.

The determined movement of the tracker 30 may be indicative of a rotation of the tracker 30, for example a clockwise or a counter-clockwise rotation (e.g., as observed by the tracking system 10). The movable portion 24 may move during the image acquisition process for acquiring the image data (e.g., triggered in step 202) such that the tracker 30 rotates and optionally translates in space (e.g., along the movement path).

Determining the movement of the tracker 30 may comprise virtually connecting the plurality of different poses of the tracker 30 as indicated by the tracking information. The movement direction may be determined based on the different points in time associated with said plurality of different poses of the tracker 30. The movement of the tracker 30 may be determined by a machine vision algorithm based on at least the tracking information. The machine vision algorithm may be configured to isolate poses of the tracker 30 from poses of other tracked trackers 32, 34, may be configured to filter out outlier poses (e.g., due to tracking errors) of the tracker 30 and/or may be configured to interpolate, average and/or extrapolate between two or more of the plurality of different poses of the tracker 30.

In optional step 210, at least one setup of the medical imaging apparatus 18 is obtained.

The at least one setup may comprise a start pose and/or an end pose of the movable portion 24 of the medical imaging apparatus 18. The start pose and/or end pose may be defined relative to an operating room, relative to the immovable portion 22 of the medical imaging apparatus 18, and/or relative to a component having a fixed spatial relationship to the immovable portion 22 of the medical imaging apparatus 18. The start pose may correspond to a pose of the movable portion 24 at a beginning of the image acquisition process and the end pose may correspond to a pose of the movable portion 24 at an end of the image acquisition process. Examples of start and end poses include a pose in which the detector 28 of the medical image acquisition apparatus 18 is in an uppermost ("12 o'clock") location, a pose in which the detector 28 of the medical image acquisition apparatus 18 is in a leftmost ("9 o'clock") location, a pose in which the detector 28 of the medical image acquisition apparatus 18 is in a lowermost ("6 o'clock") location and a pose in which the detector 28 of the medical image acquisition apparatus 18 is in a rightmost ("3 o'clock") location.

The at least one setup may be obtained by determining the at least one setup based on the tracking information, and, optionally, based on the gravity information and/or the determined movement of the tracker 30. For example, the start pose may be determined by comparing an earliest tracked pose of the tracker 30 with one or more later ones of the plurality of different poses of the tracker 30. As another example, the end pose may be determined by comparing a latest tracked pose of the tracker 30 with one or more earlier ones of the plurality of different poses of the tracker 30. The gravity information may be used to avoid ambiguity (e.g., differentiate a topmost location from a lowermost location), which may be particularly advantageous if the tracking system 10 (e.g., the camera 12) can be arranged in different orientations relative to the gravitational direction 16. The start pose and/or end pose may also be derived from the determined movement.

In optional step 212, a spatial relationship between the tracker 30 and the movable portion 24 is determined.

The spatial relationship between the tracker 30 and the movable portion 24 is determined based on at least the determined movement of the tracker.

The spatial relationship between the tracker 30 and the movable portion 24 may comprise a side (e.g., one of the multiple sides) of the movable portion 24 at which side the tracker 30 was and/or is arranged (e.g., during the movement of the tracker 30 through the plurality of different poses and/or during the image acquisition process for acquiring the image data).

As mentioned above, the determined movement of the tracker may be indicative of a movement direction of the tracker. In this case, the side of the movable portion 24 may be determined based on the movement direction of the tracker 30. In one variant, the side of the movable portion 24 is determined by selecting the side of the movable portion 24 from a first side (e.g., a right side) of the movable portion 24 associated with a clockwise movement direction of the tracker 30 and a (e.g., opposite) second side (e.g., a left side) of the movable portion 24 associated with a counter-clockwise movement direction of the tracker 30. The association(s) between the respective side(s) and the movement direction(s) of the tracker 30 may be predefined, obtained from the medical imaging apparatus 18 and/or input by a user. These association(s) may be specific for the medical imaging apparatus 18.

The side of the movable portion 24 may be determined based on the movement direction of the tracker 30 and the obtained at least one setup of the medical imaging apparatus 18. The side of the movable portion 24 may be determined by selecting, based on the determined movement direction of the tracker 30 and the obtained at least one setup of the medical imaging apparatus 18, the side of the movable portion 24 from a first side (e.g., the right side) and a second side (e.g., the left side). The first side of the movable portion 24 may be associated with (i) a clockwise movement direction of the tracker 30 and a first setup of the medical imaging apparatus 18 and/or with (ii) a counter-clockwise movement direction of the tracker 30 and a second setup of the medical imaging apparatus 18. The second side of the movable portion 24 may be associated with (i) a clockwise movement direction of the tracker 30 and the second setup of the medical imaging apparatus 18 and/or with (ii) a counter-clockwise movement direction of the tracker 30 and the first setup of the medical imaging apparatus 18. The association(s) between the respective side(s), the movement direction(s) of the tracker 30 and the setup(s) may be predefined, obtained from the medical imaging apparatus 18 and/or input by a user. These association(s) may be specific for the medical imaging apparatus 18.

The spatial relationship may comprise a location of the movable portion 24 at which location the tracker 30 was and/or is arranged (e.g., during the movement of the tracker 30 through the plurality of different poses and/or during the image acquisition process for acquiring the image data). As mentioned above, the determined movement of the tracker 30 may be indicative of a movement path of the tracker 30. In this case, the location of the movable portion 24 may be determined based on the movement path of the tracker 30.

For example, the movement path of the tracker 30 may be compared with a plurality of predefined movement paths associated with different predefined locations of the movable portion 24 at which predefined locations the tracker 30 can be arranged, to determine the location of the movable portion 24 at which location the tracker 30 was and/or is arranged. In case the movement path of the tracker 30 comprises at least one section of a circle, ellipse or helix, the location of the movable portion 24 may be determined based on the at least one section of the movement path of the tracker 30 (e.g., by comparing said at least one section to the plurality of predefined movement paths). The movement path or the at least one section may be compared to the plurality of predefined movement paths by a curve matching algorithm such as an Affine Curve Matching Algorithm, ACMA, and/or using the Fast Marching Method, FMM.

It may also be possible to determine the location without comparison to predefined movement paths, for example by mapping the movement path or the at least one section to a predefined geometrical model of the movable portion 24 or of the overall medical imaging apparatus 18.

The spatial relationship may comprise an orientation of the tracker 30 relative to the movable portion 24. As mentioned above, the determined movement of the tracker 30 may be indicative of a rotation of the tracker 30. In this case, the orientation of the tracker 30 relative to the movable portion 24 may be determined based on the rotation. It may be desirable to determine the orientation of the tracker 30 further based on the at least one setup of the medical imaging apparatus 18.

In step 214, (e.g., only or exactly) one of a plurality of transformations between a pose of the tracker 30 and the coordinate system associated with the image data acquired by the medical imaging apparatus 18 is selected.

The one of the plurality of transformations is selected based on at least the determined movement of the tracker 30.

One or more (e.g., each) of the plurality of transformations may be predefined. One or more (e.g., each) of the plurality of transformations may be specific for one or more of the medical imaging apparatus 18, the tracker 30, the mounting assembly, and combinations thereof. One or more (e.g., each) of the plurality of transformations may be stored in the memory 6.

Each of the plurality of transformations may be associated with a different (e.g., possible) predefined movement of the tracker 30. The one of the plurality of transformations may be associated with a predefined movement of the tracker 30 that matches (e.g., at least to a predefined amount) the determined movement of the tracker 30.

The one of the plurality of transformations may be selected further based on one or more inputs selected from: (i) the determined spatial relationship between the tracker 30 and the movable portion 24; (ii) the gravity information; (iii) the movement of the tracker 30 determined relative to the gravitational direction 16; (iv) the at least one setup of the medical imaging apparatus 18. Each of the plurality of transformations may be associated with one or more different (e.g., possible) predefined criteria that are selected from: (i) a predefined spatial relationship between the tracker 30 and the movable portion 24; (ii) predefined gravity information; (iii) a predefined movement of the tracker 30 relative to a predefined gravitational direction; (iv) at least one predefined setup of the medical imaging apparatus 18. The selected one of the plurality of transformations may be associated with one or more predefined criteria that match(es) (e.g., at least to a predefined degree) the one or more inputs. Such a selection may be referred to as a "direct" selection based on the one or more inputs as such. Alternatively, the one of the plurality of transformations may be "indirectly" selected based on information derived from the one or more inputs, for example based on the side of the movable portion 24 that may be determined based on the movement direction of the tracker 30 and, optionally, the at least one setup. Combinations of using an input directly and another input indirectly for selecting the one transformation are also possible.

The method may further comprise determining a relative pose between the coordinate system of the image data and the tracking coordinate system based on the selected one transformation and optionally further based on the pose of the tracker in the tracking coordinate system. A registration between the image data and a real-world coordinate system such as the tracking coordinate system may be determined based on the selected one transformation. Step 214 may comprise determining said registration based on the selected one transformation.

In optional step 216, display of a navigation view is triggered.

The navigation view may be triggered to be displayed on the display unit 38. The navigation view may be generated based on the one transformation selected in step 214. The navigation view may be indicative of a tracked pose of the medical instrument 36 relative to the medical image 42. For example, the 40 trajectory of the instrument 36 may be overlaid onto the medical image 42 to generate the navigation view. The details of how such a navigation view can be generated once the one transformation between a pose of the tracker 30 and the coordinate system associated with the image data acquired by the medical imaging apparatus 18 is selected will be apparent to those skilled in the art.

Exemplary details and implementation options of the technique disclosed herein, including the method of FIG. 2, will now be described with reference to FIGS. 3-5*c*.

Figure 3:
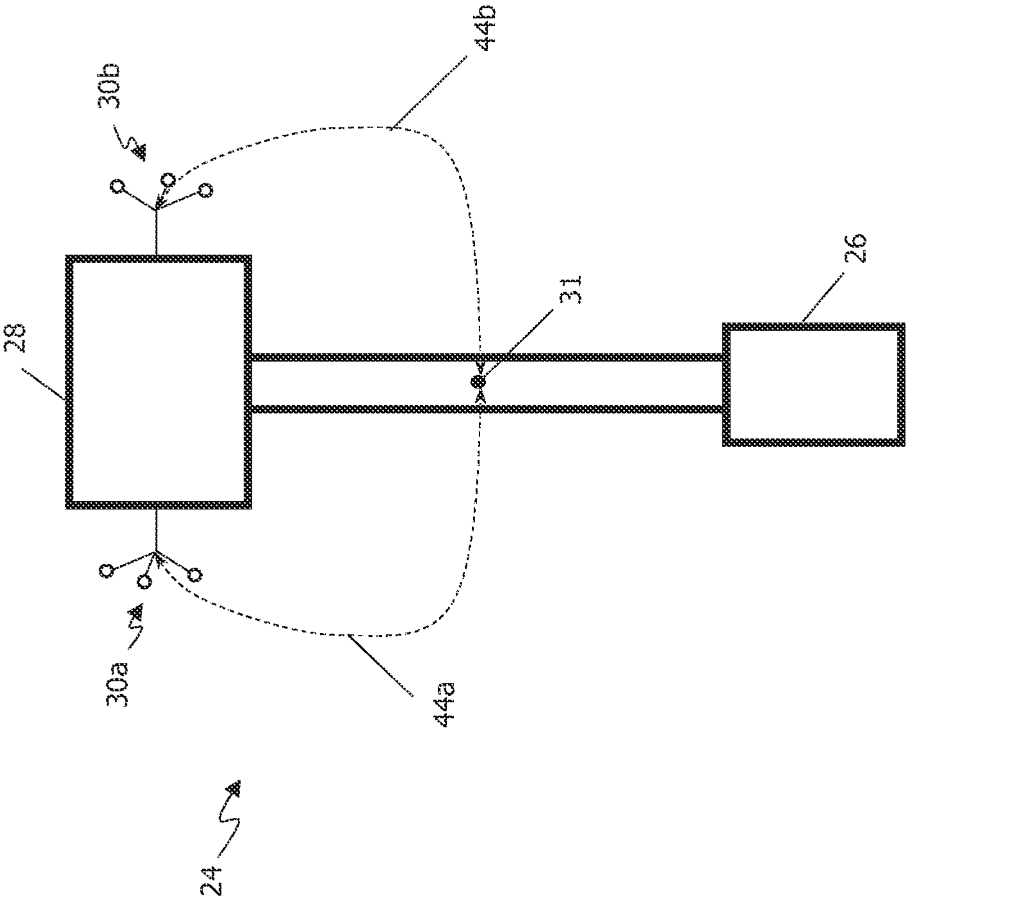
FIG. 3 illustrates different mounting arrangements of a tracker on a C-arm.

FIG. 3 illustrates different mounting arrangements of a tracker on a C-arm.

The tracker 30 may be arranged on the left side of the detector 28, resulting the arrangement designated with reference sign 30*a*. The tracker 30 may alternatively be arranged on the right side of the detector 28, resulting the arrangement designated with reference sign 30*b*. As can be seen, different predefined transformations 44*a*, 44*b* are required to describe a spatial relationship between the respective tracker arrangement 30*a*, 30*b* and the isocenter 31 lying between the detector 28 and the X-ray source 26. In case only a single pose of the tracker 30 is obtained, it may not be possible to unambiguously determine which of the transformations 44*a*, 44*b* to use. The present technique relies on determining the movement of the tracker 30 based on the tracking information to select a suitable transformation.

Figure 4B:
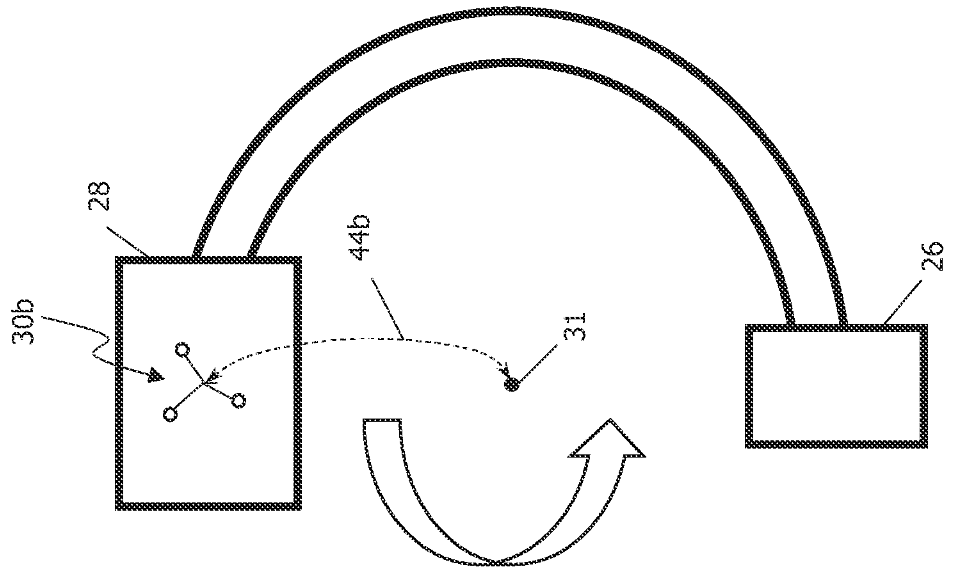
FIGS. 4*a*-4*b* illustrate side views of the different mounting arrangements of FIG. 3.
Figure 4A:
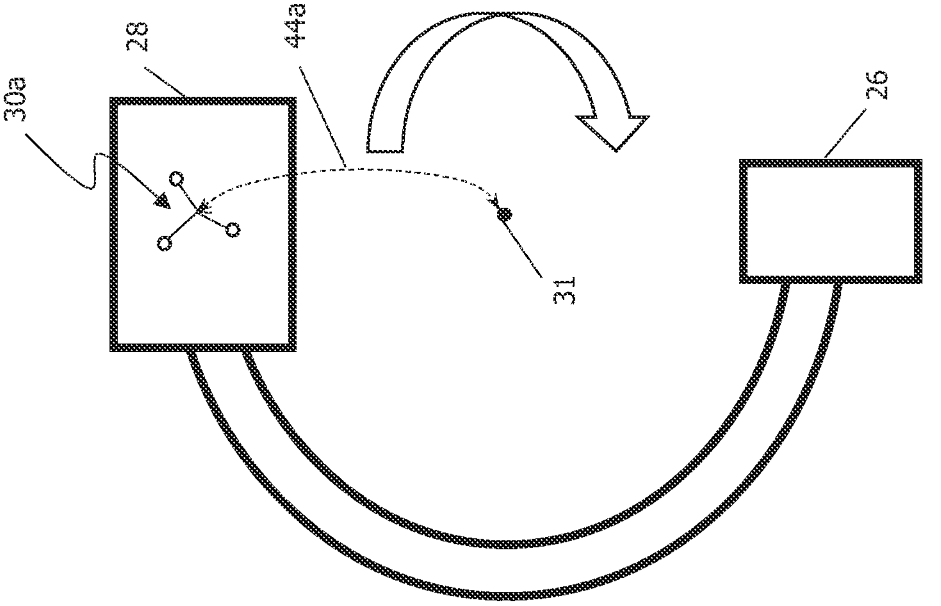

FIGS. 4*a*-4*b* illustrate side views of the different mounting arrangements of FIG. 3. In the illustrated example, the detector 28 is in a topmost 12 o'clock location at the beginning of the image acquisition process, and the C-arm has a predefined movement direction, indicated by large arrows, in which the movable portion 24 moves during the acquisition of a CT scan. In this case, if it is determined that the tracker 30 moves in the clockwise direction, it can be derived that the tracker is arranged at the left side of the C-arm according to the arrangement 30*a*, and, thus, the correct transformation 44*a* can be selected. On the other hand, if it is determined that the tracker 30 moves in the counter-clockwise direction, it can be derived that the tracker is arranged at the right side of the C-arm according to the arrangement 30*b*, and, thus, the correct transformation 44*b* can be selected.

The same approach is also possible when considering a rotation direction of the tracker 30 instead of a movement direction thereof, as a clockwise movement of the movable portion 24 will also result in a clockwise rotation (and optionally a clockwise translation) of the tracker 30.

Still further, depending on a radius of the movement path of the tracker 30 around the isocenter 31, a location at which the tracker 30 is arranged on the detector 28 can be determined. A suitable transformation can then be selected from a plurality of predefined transformations associated with different locations at which the tracker 30 can be arranged on the detector 28.

Some C-arms may be manually reconfigured, resulting in a reversal of the predefined movement directions shown in FIGS. 4*a* and 4*b*. In these cases, the predefined movement directions may still be specific for different combinations of the side of the movable portion 24 at which the tracker 30 is arranged and the start and/or end pose of the movable portion 24. Thus, even in case a C-arm is manually reconfigured, the technique disclosed herein may enable unambiguously selecting the correct transformation by further considering the start and/or end pose in addition to the movement of the tracker 30.

Figure 5A:
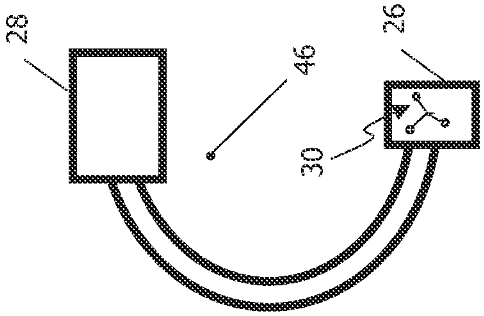
FIGS. 5*a*-5*c* illustrate different medical imaging apparatuses with trackers.

As indicated in FIG. 5*a*, the coordinate system of the image data need not be defined by the isocenter 31, but may be defined by an (e.g., arbitrarily selected) spatial position 46 that may even lie outside a volume captured by the medical imaging apparatus 18 when acquiring the image data. This spatial position may have a predefined spatial relationship relative to the movable portion 24. It is also shown that the tracker 30 may be arranged at the X-ray source 26 instead of the X-ray detector 28.

Figure 5B:
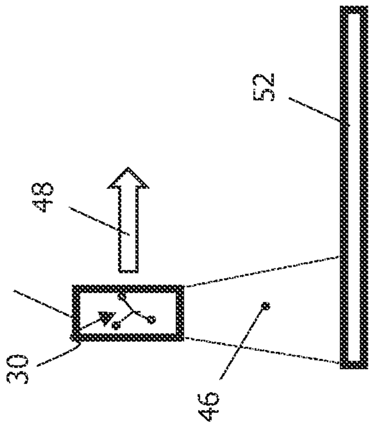

As shown in FIG. 5*b*, the present disclosure is not limited to a medical imaging apparatus 18 in which the movable portion 24 moves along a circular movement path. Instead, the movable portion 24 may move along a linear movement path 48 when the medical imaging apparatus 18 is performing the image acquisition process. Furthermore, the tracker 30 may be arranged on an emitter 50 used in the image acquisition process, instead of an X-ray detector 28. A detector 52 used in the image acquisition process may be part of the immovable portion 22 of the medical imaging apparatus 18. It is also possible that the movable portion 24 comprises a detector and the immovable portion 22 comprises a detector, each configured to be used in the image acquisition process.

Figure 5C:
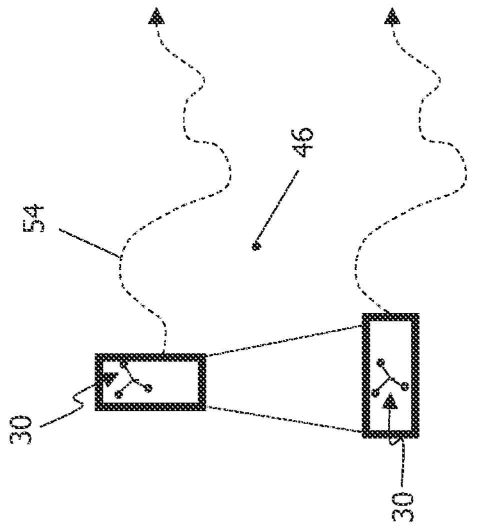

As shown in FIG. 5*c*, the movable portion 24 may be configured to move along a movement path that is neither linear nor circular, but has an arbitrary (e.g., two-dimensional and/or three-dimensional) shape that may or may not be predefined. It is also possible to select the one transformation not only based on the determined movement of a single tracker 30, but based on the determined movements of multiple trackers 30 that may each be attached to different parts of the movable portion 24, as exemplarily illustrated in FIG. 5*c*. This approach may not only improve reliability due to redundancy but may be advantageous in case the movable portion 24 changes its shape during the image acquisition process.

Various other modifications of the technique disclosed herein are possible. For example, the variants discussed for FIGS. 5*a*-5*c* may be combined with one another and/or with the configuration as shown in FIG. 1. The technique disclosed herein is not limited to an optical tracking system. Other tracking modalities may be used instead. For example, the tracking system 10 may be an electromagnetic tracking system comprising a field generator and using one or more electromagnetic field sensors as trackers. The technique disclosed herein is not limited to medical imaging apparatuses configured to acquire X-ray images. For example, the medical imaging apparatus 18 may be configured to acquire magnetic resonance, MR, image data, ultrasonic image data, microscopic image data, microwave image data or positron emission tomography, PET, image data. The movable portion of the medical imaging apparatus may not be part of a C-arm but may comprise one or both of an emitter and a detector of the medical imaging apparatus, which emitter and detector need not be configured for X-rays. Furthermore, the sequence of one or more method steps 202-216 may differ from that shown in FIG. 2. For example, the gravity information may only be used to determine the at least one setup in step 210, so step 206 may be performed between steps 206 and 208. Multiple steps may be performed at the same time, for example the data acquisition steps 204, 206. It is to be understood that one or more of the optional steps 202, 206, 210, 212, 216 may be performed, or even all of these steps, although this is not essential.

Details of the technique disclosed herein, including the method of FIG. 2, will now be explained in other words while referring to the reference signs used in the Figures, although these reference signs are not to be understood as limiting the following disclosure to the features described above for the respective Figures.

For registering volumetric image data acquired by a 3D C-arm scanner as medical imaging apparatus 18, the following pre-conditions may need to be met:

1. The C-Arm may need to be trackable, hence a tracker 30 may need to be attached to it, also referred to as C-arm tracker;
2. a spatial relation between the tracker 30 and a tracking coordinate system, for example defined by the patient tracker 32, may need to be determined based on the tracking data; and
3. a pre-calculated calibration matrix, also referred to as predefined transformation herein, that contains the spatial relationship between the tracker 30 and the volumetric image data, may need to be known.

In case these three conditions are met, an automatic image registration can be calculated once the resulting volumetric image data is sent to the at least one processor 4. The calibration matrix may define a transformation between the pose of the tracker 30 and the isocenter 31 of the C-arm, which is the point around which the C-Arm rotates and which may lie at the center of the resulting image volume (see, e.g., FIG. 1).

Some C-arm models offer multiple interface points to mount the tracker 30 to the C-arm. Such different mounting points may lead to different calibration matrices (see, e.g., FIG. 3). It may be desirable to determine which side of the C-arm the tracking system 10 is currently tracking to select the correct calibration matrix 44*a* or 44*b*.

Due to the relative nature of navigation tracking technology, one may not rely on information that is given in a static scenario in which neither the patient tracker 32 nor the C-arm tracker 30 are moved, since the orientation for each tracker may not be known beforehand. Instead, it is proposed to use the tracking data acquired during the image data acquisition process. When acquiring 3D volumetric image data, the 3D C-arm rotates around the isocenter 31 from its start to its end pose. Depending on the rotation direction of the C-arm tracker 30 in the tracking coordinate system while performing the image acquisition process, the side of the C-arm that is currently shown towards the camera 12 may be determined. This may enable using one tracker 30 that can be arranged in various locations at the movable portion 24 (e.g., attached to multiple adapter points on the C-arm), and selecting the correct calibration matrix 44*a*, 44*b* for the registration computation. This may enable a customer to re-mount the same tracker 30 on multiple mount points, depending on the current needs of the surgeon and/or a spatial operating room arrangement.

In order to determine the movement direction of C-arm, a continuous movement of the C-arm tracker 30 could be tracked for a specific duration, or the start point and one or multiple points during the rotation of the C-arm could be captured. These tracking points may form a section of a circle or ellipsoid.

From the circular or ellipsoid spatial path formed by the tracking points of the tracker 30, the direction of movement (e.g., clockwise or counterclockwise) may be determined. If the C-arm tracker 30 is fixed to one side of the C-arm, the determined movement direction of the tracker 30 may directly correlate to seeing a clockwise or counterclockwise rotation of the C-arm. In this case, it may be assumed that the C-arm always rotates the same way and the rotation direction for each side is known in advance. When moving and rotating the camera 12, clockwise and counterclockwise may always stay in the same relation to the C-arm side (see, e.g., FIG. 4).

The camera 12 need not be arranged such that its field of view is aligned with (e.g., parallel to or centered on) a rotation axis of the C-arm. When the camera 12 is placed in front or behind of the C-arm, the C-arm tracker 30 will move towards or away from it. As long as there is an angle different to 0 or 90 degrees between camera 12 and C-arm tracker 30, the circular or straight back/front movement will transform into an ellipsoid. By tracking this ellipsoid, not only the mounting side of the C-arm but may be determined, but it may even be possible to distinguish between different mounting points on the same side.

Some C-arms can be (e.g., manually) reconfigured by turning the "C" along the roll axis. This may result in a swapping of the relation of clockwise/counterclockwise rotation of the C-arm to the respective C-arm side. In this case, the gravitational direction 16 may be considered. Based on the gravitational direction, the start pose of the imaging apparatus 18 (e.g., the start position of the detector 28) at the beginning of the image acquisition process can be determined, as it is clear whether the detector 28 starts rotating from the top position or the lowest position. Without the gravitational direction, which clearly points towards an external reference, the camera 12 may not know how it is rotated in space, hence the absolute top and low position may not be able to be calculated, unless it is assumed that the camera 12 is always oriented in the same manner relative to the gravitational direction 16. When combining the gravitational direction and the determined movement direction of the tracker 30, different start and end poses can be determined as setups of the image acquisition apparatus 18.

The association between rotation direction and tracked C-arm side may be predefined, for example based on a calibration in which a user stores the association(s). The user may be asked to rotate the C-arm in each direction or skip it if one of the rotations is not applicable (e.g., if the C-arm does not support rotation along the roll axis). Once the associations between rotation direction and tracked C-arm side (and optionally one or more setups of the C-arm) are defined, they may be stored in the memory 6 and potentially also used for subsequent image acquisition processes.

The acquired rotational knowledge may need some error factor as there might be jittering in both, rotation as well as tracking. However, this jitter of the recorded positions may be equal between all C-arm models as the recorded curve may be detectable with any jitter and only the clockwise/counterclockwise information (and optionally the setup of the C-arm) may be relevant for determining the attachment side of the tracker 30 on the C-arm.

By having a side detection implemented, it may be possible to use one single C-arm tracker 30 to get a registered and navigable medical image, with the camera 12 being able to stand on either side of the C-arm. The tracker 30 can then be switched between different mounting points and the respective calibration based on the selected one transformation 44*a*, 44*b* may be used.

To sum up, the technique disclosed herein may allow automatically selecting a transformation between a pose of a medical imaging apparatus tracker and a coordinate system associated with image data acquired by the medical imaging apparatus. It may be possible to select said transformation based on different poses of the medical imaging apparatus tracker as tracked during an image acquisition process in which one or more medical images of a patient's body are acquired. The selected transformation may enable registering the medical image(s) to a real-world coordinate system without requiring a patient or registration phantom to be imaged. The technique may be particularly advantageous if surgeons wish to attach the medical imaging apparatus tracker to said apparatus in different mounting poses. As no user input on the mounting pose may be required, errors in the selection of the transformation may be reduced. Further advantages of the technique may be apparent to those skilled in the art.

The present disclosure also provides for the following non-limiting Examples:

Example 1: A method for selecting a transformation between a pose of a tracker (30) and a coordinate system associated with image data acquired by a medical imaging apparatus (18), the method being performed by at least one processor (4) and comprising:

obtaining (204) tracking information indicative of a plurality of different poses of a tracker (30) that is fixedly positioned relative to a movable portion (24) of a medical imaging apparatus (18);

determining (208), based on the obtained tracking information, a movement of the tracker (30); and selecting (214), based on the determined movement of the tracker (30), one of a plurality of transformations between a pose of the tracker (30) and a coordinate system associated with image data acquired by the medical imaging apparatus (18).

Example 2: The method of Example 1, further comprising:

determining (212), based on the determined movement of the tracker, a spatial relationship between the tracker (30) and the movable portion (24), wherein the one transformation is selected from the plurality of transformations based on the determined spatial relationship.

Example 3: The method of Example 1 or 2, wherein the spatial relationship comprises a side of the movable portion (24) at which side the tracker (30) is arranged.

Example 4: The method of Example 3, wherein the determined movement of the tracker is indicative of a movement direction of the tracker (30), wherein the side of the movable portion (24) is determined based on the movement direction of the tracker (30).

Example 5: The method of Example 4, wherein the side of the movable portion (24) is determined by selecting the side of the movable portion (24) from a first side of the movable portion (24) associated with a clockwise movement direction of the tracker (30) and a second side of the movable portion (24) associated with a counter-clockwise movement direction of the tracker (30).

Example 6: The method of any one of Examples 2 to 5, wherein the spatial relationship comprises a location of the movable portion (24) at which location the tracker (30) is arranged.

Example 7: The method of Example 6, wherein the determined movement of the tracker (30) is indicative of a movement path of the tracker (30), wherein the location of the movable portion (24) is determined based on the movement path of the tracker (30).

Example 8: The method of Example 7, wherein the movable portion (24) is configured to move along a circle or helix, wherein the movement path of the tracker (30) comprises at least one section of a circle, ellipse or helix and the location of the movable portion (24) is determined based on the at least one section of the movement path of the tracker (30).

Example 9: The method of any one of Examples 2 to 8, wherein the spatial relationship comprises an orientation of the tracker (30) relative to the movable portion (24).

Example 10: The method of any one of Examples 1 to 9, further comprising:

obtaining gravity information indicative of a gravitational direction, wherein the transformation is selected based on the gravity information.

Example 11: The method of Example 10, wherein the movement of the tracker (30) is determined relative to the gravitational direction as indicated by the gravity information, wherein the transformation is selected based on the movement of the tracker (30) determined relative to the gravitational direction.

Example 12: The method of any one of Examples 1 to 11, further comprising:

obtaining (210) at least one setup of the medical imaging apparatus (18) selected from a start pose and an end pose of the movable portion (24) of the medical imaging apparatus (18) relative to an immovable portion (22) of the medical imaging apparatus (18) or a component having a fixed spatial relationship to the immovable portion (22) of the medical imaging apparatus (18), wherein the transformation is selected based on the at least one setup of the medical imaging apparatus (18).

Example 13: The method of Example 12 and Example 10 or 11, further comprising:

determining the at least one setup of the medical imaging apparatus (18) based on the tracking information, the gravity information and the determined movement of the tracker (30), to obtain the at least one setup of the medical imaging apparatus (18).

Example 14: The method of Example 12 or 13 as far as depending on Example 4, wherein the side of the movable portion (24) is determined based on the movement direction of the tracker (30) and the obtained at least one setup of the medical imaging apparatus (18).

Example 15: The method of Example 14, wherein the side of the movable portion is determined by selecting, based on the determined movement direction of the tracker (30) and the obtained at least one setup of the medical imaging apparatus (18), the side of the movable portion (24) from:

- a first side of the movable portion (24) associated with (i) a clockwise movement direction of the tracker (30) and a first setup of the medical imaging apparatus (18) and (ii) a counter-clockwise movement direction of the tracker (30) and a second setup of the medical imaging apparatus (18); and
- a second side of the movable portion (24) associated with (i) a clockwise movement direction of the tracker (30) and the second setup of the medical imaging apparatus (18) and (ii) a counter-clockwise movement direction of the tracker (30) and the first setup of the medical imaging apparatus (18).

Example 16: The method of any one of Examples 1 to 15, wherein at least two or all of the plurality of different poses of the tracker (30) are associated with different points in time of an image acquisition process performed by the medical imaging apparatus (18) to acquire the image data, during which image acquisition process the movable portion of the medical imaging apparatus (18) moves.

Example 17: The method of any one of Examples 1 to 16, wherein the medical imaging apparatus (18) is configured to acquire computed tomography, CT, image data and the movable portion (24) of the medical imaging apparatus (18) is part of a C-arm.

Example 18: A system (100) comprising at least one processor (4) configured to perform the method according to any one of Examples 1 to 17.

Example 19: The system of Example 18, further comprising at least one of the following entities:

i) the medical imaging apparatus (18) comprising the movable portion (24) and configured to acquire the image data;

ii) a tracking system (10), such as an optical tracking system comprising a camera, configured to provide the tracking information;

iii) a gravity sensor (14) configured to provide the gravity information and optionally fixed to the tracking system (10) and/or the camera (12);

iv) the tracker (30).

Example 20: A computer program comprising instructions which, when executed by at least one processor (4), cause the at least one processor (4) to perform the method according to any one of Examples 1 to 17, the computer program being optionally carried by a data stream or stored on a (e.g., non-transitory computer-readable) storage medium (6).

The invention claimed is:

1. A method for selecting a transformation between a pose of a tracker and a coordinate system associated with image data acquired by a C-arm, the method being performed by at least one processor and comprising:

obtaining tracking information indicative of a plurality of different poses of the tracker that is fixedly positioned in one of at least two positions and/or orientations relative to a movable portion of the C-arm, wherein the movable portion is at least one of an x-ray source or an x-ray detector and the tracking information is generated by an optical tracking system comprising a camera;

determining, based on the obtained tracking information, a movement of the tracker;

selecting, based on a direction of the determined movement of the tracker, one of a plurality of transformations between the pose of the tracker and the coordinate system associated with the image data acquired by the C-arm; and displaying, on a display unit, a navigation view based on the selected one of the plurality of transformations.

2. The method of claim 1, further comprising:

determining, based on the determined movement of the tracker, a spatial relationship between the tracker and the movable portion, wherein the one transformation is selected from the plurality of transformations based on the determined spatial relationship.

3. The method of claim 2, wherein the spatial relationship comprises a side of the movable portion at which side the tracker is arranged.

4. The method of claim 3, wherein the side of the movable portion is determined based on the the direction of the determined movement.

5. The method of claim 4, wherein the side of the movable portion is determined by selecting the side of the movable portion from a first side of the movable portion and an opposite second side of the movable portion.

6. The method of claim 2, wherein the spatial relationship comprises a location of the movable portion at which the tracker is arranged.

7. The method of claim 6, wherein the determined movement of the tracker is indicative of a movement path of the tracker, and wherein the location of the movable portion is determined based on the movement path of the tracker.

8. The method of claim 7, wherein the movable portion is configured to move along a circle or helix, and wherein the movement path of the tracker comprises at least one section of a circle, ellipse or helix and the location of the movable portion is determined based on the at least one section of the movement path of the tracker.

9. The method of claim 2, wherein the spatial relationship comprises an orientation of the tracker relative to the movable portion.

10. The method of claim 1, further comprising:

obtaining gravity information indicative of a gravitational direction, wherein the transformation is selected based on the gravity information.

11. The method of claim 10, wherein the movement of the tracker is determined relative to the gravitational direction as indicated by the gravity information, and wherein the transformation is selected based on the movement of the tracker determined relative to the gravitational direction.

12. The method of claim 1, further comprising:

obtaining at least one setup of the C-arm selected from a start pose and an end pose of the movable portion of the C-arm relative to an immovable portion of the C-arm or a component having a fixed spatial relationship to the immovable portion of the C-arm, wherein the transformation is selected based on the at least one setup of the C-arm.

13. The method of claim 12, further comprising:

obtaining gravity information indicative of a gravitational direction relative to one or more of the plurality of different poses of the tracker; and determining the at least one setup of the C-arm based on the tracking information, the gravity information, and the determined movement of the tracker.

14. The method of claim 12, wherein:

the spatial relationship comprises a side of the movable portion at which side the tracker is arranged, the determined movement of the tracker is indicative of a movement direction of the tracker, and the side of the movable portion is determined based on the movement direction of the tracker and the obtained at least one setup of the C-arm.

15. The method of claim 1, wherein at least two of the plurality of different poses of the tracker are associated with different points in time of an image acquisition process performed by the C-arm to acquire the image data, during which image acquisition process the movable portion of the C-arm moves.

16. The method of claim 1, wherein the C-arm is configured to acquire computed tomography, CT, image data.

17. A system comprising at least one processor configured to perform a method for selecting a transformation between a pose of a tracker and a coordinate system associated with image data acquired by a C-arm, the method comprising:

obtaining tracking information indicative of a plurality of different poses of the tracker that is fixedly positioned in one of at least two positions and/or orientations relative to a movable portion of the C-arm, wherein the movable portion is at least one of an x-ray source or an x-ray detector and the tracking information is generated by an optical tracking system comprising a camera;

determining, based on the obtained tracking information, a movement of the tracker;

selecting, based on a direction of the determined movement of the tracker, one of a plurality of transformations between the pose of the tracker and the coordinate system associated with the image data acquired by the C-arm; and displaying, on a display unit, a navigation view based on the selected one of the plurality of transformations.

18. The system of claim 17, further comprising at least one of the following entities:

i) the C-arm comprising the movable portion and configured to acquire the image data;

ii) the optical tracking system comprising the camera configured to provide the tracking information;

iii) a gravity sensor configured to provide gravity information; and iv) the tracker.

19. A non-transitory computer-readable storage medium storing a computer program comprising instructions which, when executed by at least one processor, cause the at least one processor to perform a method for selecting a transformation between a pose of a tracker and a coordinate system associated with image data acquired by a C-arm, the method comprising:

obtaining tracking information indicative of a plurality of different poses of the tracker that is fixedly positioned, in one of at least two positions and/or orientations relative to a movable portion of the C-arm, wherein the movable portion is at least one of an x-ray source or an x-ray detector and the tracking information is generated by an optical tracking system comprising a camera;

determining, based on the obtained tracking information, a movement of the tracker;

selecting, based on a direction of the determined movement of the tracker, one of a plurality of transformations between the pose of the tracker and the coordinate system associated with the image data acquired by the C-arm; and displaying, on a display unit, a navigation view based on the selected one of the plurality of transformations.

* * * * *